United States Patent [19]

Roggero

[11] Patent Number: 4,680,407
[45] Date of Patent: Jul. 14, 1987

[54] CERTAIN ALKALI METAL BIS-PHENETHYL OR TRIS-PHENETHYL-PYRIDINES USEFUL AS MULTIFUNCTIONAL ANIONIC INITIATORS

[75] Inventor: Arnaldo Roggero, S. Donato Milanese, Italy

[73] Assignee: Enichem Elastomeri S.p.A., Palermo, Italy

[21] Appl. No.: 677,344

[22] Filed: Dec. 3, 1984

[30] Foreign Application Priority Data

Dec. 5, 1983 [IT] Italy ............................... 24019 A/83

[51] Int. Cl.⁴ .......................................... C07D 213/24
[52] U.S. Cl. ................................... 546/348; 526/180; 526/258; 546/291
[58] Field of Search ......................................... 546/348

[56] References Cited

U.S. PATENT DOCUMENTS 4,450,259 5/1984 Roggero et al. .................... 526/173

Primary Examiner—Alan L. Rotman
Attorney, Agent, or Firm—Birch, Stewart, Kolasch & Birch

[57] ABSTRACT

Multifunctional anionic initiators of the general formula

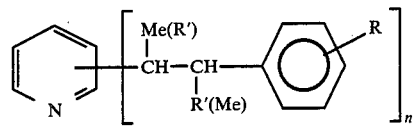

Process for their synthesis, and use of them in polymerization processes.

7 Claims, No Drawings

CERTAIN ALKALI METAL BIS-PHENETHYL OR TRIS-PHENETHYL-PYRIDINES USEFUL AS MULTIFUNCTIONAL ANIONIC INITIATORS

Anionic polymerization, if is carried out under suitable experimental consitions and with well determined monomers, allows polymers to be obtained having well defined structure. In this sense, particular attention has been paid to the synthesis of block polymers, with special reference to those on the basis of dienes and of vinylaromatic monomers, of functionalized telechelic polymers, and of polymers deriving from these by means of further modifications, or of polymerization with monomers also different from those mentioned above.

For the purpose of obtaining polymers having good characteristics, it is however necessary to use particular catalysts, whose more important requisites may be summarized as follows:

(i) rigorously defined functionality;
(ii) solubility in hydrocarbon solvents;
(iii) good stability.

The easiness of their synthesis and an easy availability are then as important features as those mentioned.

The well defined functionality is an essential requisite for the synthesis of homogeneous polymer structures, to which outstanding physical characteristics correspond.

Sometimes indeed the multifunctional catalysts do not show a univocal structure, in that products coexist contemporaneously having different functionality and this leads as a consequence to heterogeneous polymeric products with unsatisfactory properties.

The solubility in hydrocarbon solvents is also an equally important requisite in that, in the polymerization of conjugated dienic monomers, it allows dienic structures to be obtained with a high level of 1-4 interconnection (the presence of polar solvents would have indeed a negative influence) and the polymers to the obtained with the desired molecular weight.

The good stability of the catalysts is important too to the purpose of controlling the molecular weight and of preparing homogeneous products, while at last their easy availability is important from the economical point of view.

The multifunctional catalysts (i.e., with a functionality of not less than 2) presently known exhibit all the favourable characteristics as described above with difficulty (see e.g., D. H. Richard, Development in Polymerization, Chapter 1, Ed. R. N. Haward, Appli. Sci. Publ. Ltd., England), whilst all these favourable characteristics and other advantages, as it shall be clarified hereunder, are obtained by means of the catalytic systems disclosed herein.

It is therefore a first object of the instant invention to provide a class of muntifunctional anionic initiators of general formula (I)

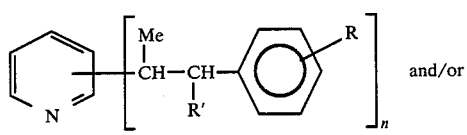 and/or (I)

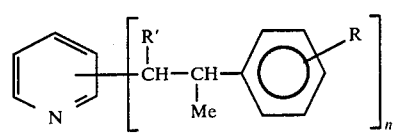

in which:
Me=Alkaline metal
n=an integer of 2 to 5, and preferably with the value of 2 or 3.
R'=alkyl group, amide group and hydrogen
R=hydrogen, an alkyl radical (having preferably a tertiary carbon atom directly bound to the aromatic ring), a cycloalkyl group, an alkoxy group and an aromatic radical. It comprises from 0 to 18 carbon atoms.

The initiators (I) are prepared by introducing metal atoms in products of general formula (II):

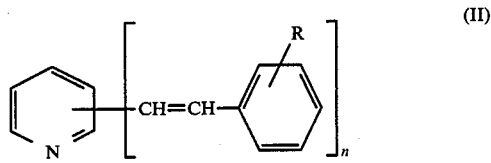

(II)

where R and n have the meanings as defined above.

Such base compounds can be synthesized according to the methods known from technical literature, e.g. by starting from methyl derivatives of pyridine, in a simple way and with yields which in some cases can also be quantitative, according to the process by A. E. Siegrist et al. (Helv. Chim. Acta, 63 (5), 1311, 1980):

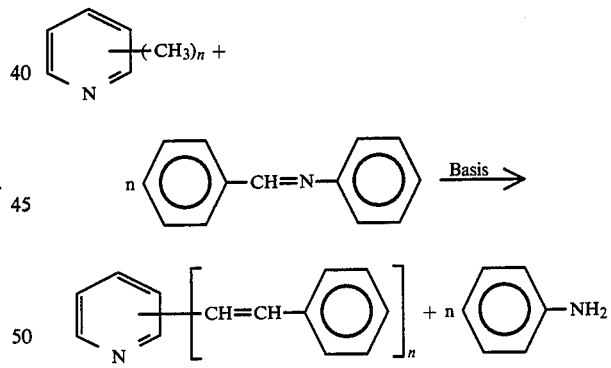

Typical examples of methyl compounds used are the 2,6-dimethylpyridine, 2,4-dimethylpiridine and 2,4,6-trimethylpyridine.

To polistyryl compounds (II) are then added alkyl compounds, amide compounds or hydrides of alkaline metals MeR' or MeNR₂" or MeH (preferably the lithium alkylates), which by linking themselves to the unsaturated bonds existing in the base compounds (II) form the catalysts of general formula (I).

The lithium alkylates generally used are monoalkylates, with from 1 to 12 carbon atoms: methyl-lithium, ethyl-lithium, n.propyl-lithium, isopropyl-lithium, n.butyl-lithium, isobutyl-lithium, sec.butyl-lithium, tert.butyl-lithium, n.amyl-lithium, isoamyl-lithium, sec.amyl-lithium, and tert.amyl-lithium. The secondary and tertiary compounds are those to be preferred. Also lithium alkylarylates compounds can be used, such as: benzyllithium, 1-lithium-ethylbenzene, and 1-lithium-3-methylpentylbenzene (addition product of sec.butyl-lithium to styrene).

The ratio between these and the base compound (II) depends on the type of catalyst desired.

The formation reaction of the catalyst is carried out in the presence of aliphatic, cycloaliphatic, aromatic, alkylaromatic solvents, or their mixtures, at a temperature within the range of from 0° C. to 80° C.

As solvents preferably used are n-pentane, n-hexane, n-heptane, cyclohexane, methylcyclohexane, benzene, toluene, xylene, ethylbenzene and pseudocumene.

In the reaction medium also additives may be present, such as amines, preferably tertiary amines, in a variable ratio with the alkaline metal: Me/N=1/0,1 to 1/1.

Also additives may be used of the ether type under such conditions as to avoid secondary reactions between the metal bearing compounds and the ether itself.

The addition e.g. of two molecules of Me—R' to the compound containing two

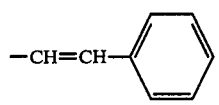

groups (DIF), allows anionic perfectly difunctional catalysts to be obtained, as well as the addition of three molecules of MeR' to the compound containing three

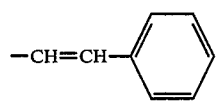

groups (TRIF), allows anionic perfectly trifunctional catalysts to be obtained, etc.

Moreover, by starting from compounds of the type (I), it is possible to achieve catalysts with a functionality higher than n, as it is shown thereafter, in which x=pyridine group.

MeR' + DIF ⟶

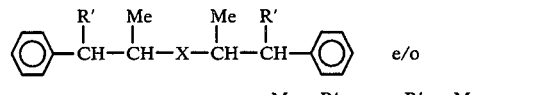

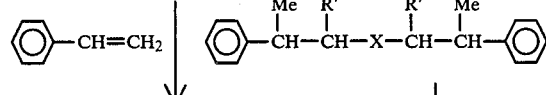

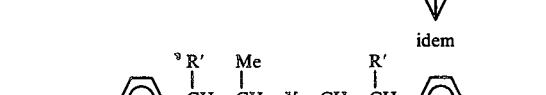

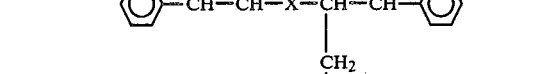

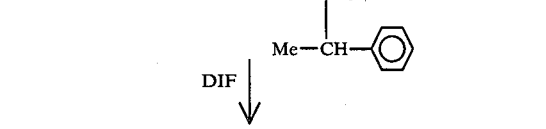

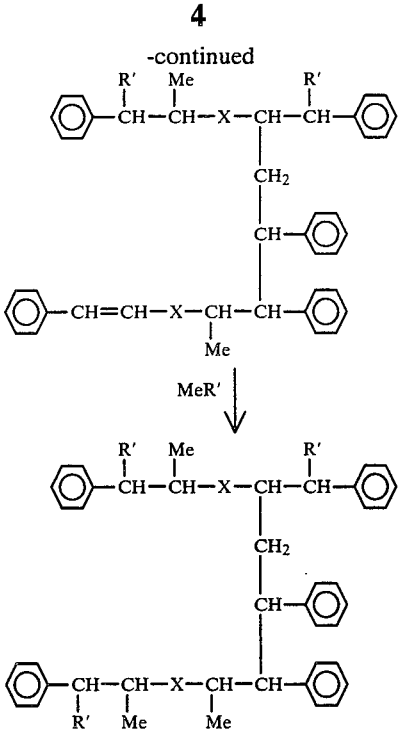

It is therefore a second object of the instant invention, to provide a class of anionic initiators with functionality higher than n, deriving from the compounds of formula (II).

The catalysts disclosed herein are soluble in aromatic, cycloaliphatic, aliphatic solvents and in their blends, even without any additions of polar solvents.

Sometimes, before being stored, the catalysts of the invention are reacted with polymerizable compounds (P) of diene type and/or of vinylaromatic type, leading to structures (in the case of bifunctional compounds) of the type:

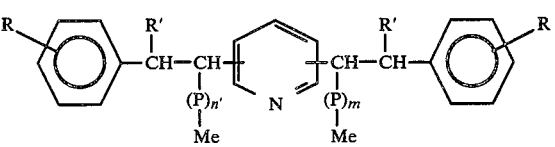

and/or

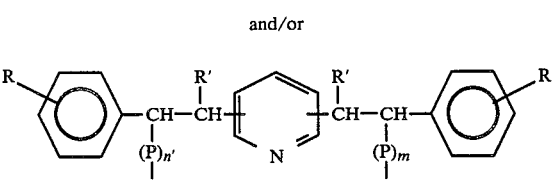

in which:

$n' + m = 20$, and in general for different structures, about 10 molecules of P are provided per each gram atom of Me.

The values of n' and m may be within a broad range (from 1 to 50).

The catalysts which are the object of the present invention have excellent stability, and very good solubility characteristics in the hydrocarbon solvents used.

Such catalysts may be used for processes of homopolymerization, statistic polymerization, especially for compounds of homogeneous classes, or of block copolymerization, also for compounds of non homogeneous classes, depending on whether in the polymerization environment such compounds are charged all together, or according to a sequential fashion, as conjugated dienes, vinylaromatic compounds, esters, nitriles, N,N-disubstituted amides of acryl and methacryl compounds, vinylpyridines, vinylquinolines and their derivatives, episulphides, epoxides, lactones, lactams, siloxanes and more generally all those compounds which are liable of anionic initiation.

Generally as dienes 1,3-butadiene, isoprene, 2,3-dimethyl-1,3-butadiene, 1,3-pentadiene (piperylene), 2-methyl-1,3-hexadiene and 3-butyl-1,3-octadiene are used.

Also alkoxy- and halogen-substituted dienes may be used, such as 2-methoxy-1,3-butadiene, chloroprene, fluoroprene. As vinyl aromatic compounds: styrene, α-methylstyrene, α-p.dimethylstyrene, 1-vinylnaphthalene, 2-vinylnaphthalene, 4-phenylstyrene, 2-isopropenylnaphthalene, 4-phenyl-α-methylstyrene and other compounds with different substituting groups on the aryl ring of the alkyl, cycloalkyl, aryl, alkylaryl, alcoxyl, aryloxyl, dialkylamino types may be used. As episulphides: ethylenesulphide, propylenesulphide, isobutenesulphide, 1-allyloxy-2,3-epithiopropane; as epoxides: ethyleneoxide; as lactones: pivalolactone; as lactams: caprolactam; and as siloxanes: hexamethylcyclotrisiloxane and octamethylcyclotetrasiloxane may be used.

The polymerization of such monomers takes place generally in solvents selected from aliphatic and cycloaliphatic hydrocarbons (pentane, hexane, heptane, cyclohexane), aromatic and alkylaromatic hydrocarbons (benzene, toluene, xylene), polar aprotic compounds (dimethylether, dioxane, tetrahydrofuran, furan, dimethoxyethane, diethyleneglycol dimethylether, hexamethylphosphoramide), at a temperature within the range of from $-78°$ C. up to the decomposition temperature of obtained polymers.

The polymerization may also be conveniently carried out in the absence of any solvents.

Without the structure of polydiene appearing to be substantially changed, also limited amounts (at least up to 10/1=compound/alkaline metal) may be used, together with the above mentioned solvents, of trialkylamines, dialkylarylamines, diarylethers and alkylarylethers.

As these polymerization processes are "living" polymerizations, the concentration of the catalyst depends on the molecular weight of desired product.

The polymers containing —C—Me active bonds can be treated with several agents, which change these active bonds into functional groups: examples of such functionalizing agents are: ethyleneoxide, styreneoxide, ethylenesulphide, oxygen, carbon dioxide, ethyl chloroformate, allyl halogenides, succinic anhydride and maleic anhydride, phosgene, thionyl chloride, toluene-2,4-diisocianate, and so on. In the present case, the perfect functionality allows polymeric structures to be obtained with a well defined number of functional end groups, with evident advantageous effects on the properties of such structures, and/or of the structures resulting from the graft polymerization from the same functional groups.

EXAMPLES 1 to 12

All working details will be clear from the reading of the following Examples. The Examples however shall not be constructed as being in any way limitative of the invention herein disclosed.

SYNTHESIS OF MULTIFUNCTIONAL ANIONIC INITIATORS

Example 1

The process is carried out within a 250 cm$^3$ flask equipped with stirrer, dropping funnel, nitrogen inlet, and inlet for feeding the reactants. 5 mmole of 2,6-distyrylpyridine dissolved in 100 cm$^3$ of benzene are introduced, and 10 mmole of lithium-sec.butyl are slowly added dropwise, at the temperature of $-5°$ C.

After about one hour, the intensely coloured solution (CAT A) is divided into two equal parts (3 g), and left for one hour at the temperature of 60° C. The product obtained (CAT A') is subsequently used for the polymerization tests.

A second part is treated with methanol and the isolated organic product is submitted to the M.S. and $^1$H-NMR analyses. The data from the mass analysis show the prevailing presence of a compound with molecular weight of 399, deriving from the addition of two sec.butyl groups to a molecule of distyrylpyridine. The data from $^1$H-NMR confirm the total disappearance of the vinyl unsaturations and the concomitant addition of the sec.butyl saturated groups.

Example 2

The reaction is carried out as previously described, but using cyclohexane as solvent, and operating at about 70° C. In two hours, the CAT B is obtained, which, at the M.S. and $^1$H-NMR analyses still shows the perfect addition of two sec.butyl groups to the molecule of 2,6-distyrylpyridine.

Example 3

2,4-Distyrylpyridine is used (5 mmole) carrying out the reaction in benzene (50 cm$^3$) at room temperature. In the usual equipment 10 mmole of lithium sec.butyl are added, together with 1 mmole of triethylamine. After 2 hours, an intensely coloured product (CAT C) is obtained, which contains two sec.butyl groups per molecule of distyrylpyridine.

Example 4

In the equipment of Example 1, 10 mmole are introduced of 2,4,6-tristyrylpyridine, 200 cm$^3$ of benzene and 30 mmole of lithium-sec.butyl containing 6 mmole of dimethylaniline. The reaction is carried out at room temperature for 2 hours (CAT D), and at M.S. and $^1$H-NMR analyses (on the product quenched with CH$_3$OH), there is evidence of the addition of 3 sec.butyl groups to the starting compound.

POLYMERIZATION

Example 5

In a glass reactor of 1 liter capacity, completely airfreed, equipped with air-tight stirrer, temperature and pressure indicators, and reactant introduction inlet, 600 cm$^3$ of anhydrous benzene and 1,2 mmole of CAT A' (2,4 meq of Li) are introduced. 42 g of butadiene are subsequently introduced, leaving the mixture to polymerize at 60° C. for 1 hour.

One sixth of this polymeric solution is placed inside a reactor with a nitrogen blanket, and to it 1 cm$^3$ of tetrahydrofuran and 0,4 meq of SiCl$_4$ are added. A gel is immediately formed, and after 20 minutes of stirring at room temperature, glacial acetic acid is added, leaving the gel containing mixture at room temperature overnight. The polybutadiene shows a gel content of 70% by weight, thus confirming the difunctional nature of CAT A'.

To the five sixths of the polymeric solution styrene (15 g) is added, and they are allowed to polymerize at 70° C. for 2 hours. The polymer is quenched with methanol, coagulated and dried. A quantity of 51 g of product is isolated, which at $^1$H-NMR analysis shows a styrene content of 29,5% by weight, and the residual polybutadiene shows a prevailingly 1,4 structure.

The DSC analysis of the polymers shows two transitions to be attributed to the polybutadiene block ($-86°$ C.) and to the polystyrene block ($+98°$ C.). The molecular weight Mn is about 102.000 and the ratio Mw/Mn is 1,36.

Example 6

The polymerization is carried out as shown in Example 5, with the only difference that the catalyst B is used. The results are the same.

Example 7

In a glass bottle of the capacity of 150 cm$^3$, 25 cm$^3$ of cyclohexane, 25 cm$^3$ of α-methylstyrene (α-STY), 0,5 cm$^3$ of styrene and 10,4 g of butadiene are charged. At room temperature, 0,4 meq of CAT A interreacted at room temperature with 0,4 meq of dimethylether are introduced by means of a perfectly tight syringe. After 8 hours of reaction at room temperature, 15,4 g of a polymer are isolated by precipitation with methanol and drying under vacuum, such polymer at the examination by $^1$H-NMR shows the following composition: α-STY=32,5% by weight. The polybutadiene (67,5% by weight) has a prevailingly 1,4-structure.

The Differential Thermal Analysis shows two transitions, at $-82°$ C. and at $+170°$ C. (not well defined), to be attributed to the two blocks. The molecular weight Mn of the product is about 100.000, and its mechanical properties are: at 24° C., for an elongation (at breakdown) of 550%, the tensile strength is of 18 MPa; at 100° C., for an elongation (at breakdown) of 600%, the tensile strength is of 9 MPa.

Example 8

In a blend of tetrahydrofuran (25 cm$^3$) and methylcyclohexane (25 cm$^3$) are charged 10 g of butadiene and 4 g of 2-isopropenylnaphtalene (2-IPN).

The catalyst CAT C (0,4 meq) is introduced, and the mixture is made to polymerize for several hours, thus 14 g being obtained of a polymer, whose composition is 2-IPN=28,5% by weight. The polybutadiene has high values of 1,2-interconnections. Such a product is hydrogenated under such conditions as to essentially modify the dienic unsaturation. The $^1$H-NMR analysis confirms the total disappearance of the unsaturations, and the DSC analysis shows the transitions at $-60°$ C. to be attributed to the C$_2$–C$_4$ copolymer, and at $+220°$ C., to be attributed to poly2-IPN.

The properties of this product, including also the thermooxidative stability, are outstanding.

Example 9

Using CAT A' (0,5 meq) the butadiene (10 g) is polymerized in a benzene solution (100 cm$^3$) at the temperature of $+60°$ C. The polymer obtained is siphoned into a mixture of benzene and tetrahydrofuran saturated with carbon dioxide, and is made react at the temperature of $-5°$ C. for 1 hour. The mixture is then slightly acidified, isolating a polymer which shows (IR data) to contain evident quantities of carboxyl groups. The molecular weight Mn is close to 80.000, and the microstructure has a high 1-4 content (88% molar).

Such product is dissolved in a blend 1/1 (v/v) of toluene and tetrahydrofuran (200 cm$^3$), and to it 0,3 meq are added of hydroxide of tetrabutylammonium. The mixture is allowed to react for 15' at the temperature of 60° C., and then 3g are added of pivalolactone. After 2 hours 13 g are isolated, by acidification with HCl, and precipitation with methanol, of a product containing 23% by weight of polypivalolactone.

The DTA shows for this polymer two transitions at $-84°$ C. and at $+270°$ C., to be attributed respectively to the high (1-4) polybutadiene and to polypivalolactone.

Example 10

The above test is repeated by using the catalyst CAT D, and using as the solvent a blend of 100 cm$^3$ of benzene-tetrahydrofuran (1/1 v/v).

The polymerization is carried out as described above, and after having isolated the COOH-functionalized product, the hydrogenation is carried out, thus a polymer being obtained, which at the $^1$H-NMR analysis no longer contains any unsaturations, and which, at the DSC examination shows a transition at $-58°$ C., to be attributed to the copolymer C$_2$–C$_4$.

This product is treated in the same way as the preceding with pivalolactone, thus a polymer being finally obtained, which shows interesting properties, with particular reference to the thermooxidative stability.

Example 11

In a mixture of tetrahydrofuran (50 cm$^3$), hexamethylphosphoramide (2 cm$^3$), 30 mmole of ethylenesulphide, 64 mmole of propylenesulphide and 6 mmole of 1-allyloxy2,3-epithiopropane are added at the temperature of $-30°$ C. 0,1 mmole of CAT C are added, allowing the polymerization to proceed at room temperature for 8 hours. The completely amorphous at X-rays terpolymer is isolated with quantitative yields.

After curing at 145° C. for 60' (filled with HAF carbon black), elongations (at breakdown) of 700% and corresponding tensile strengthes of 20 MPa are obtained. Such products demonstrate good properties of resistance to solvents.

Example 12

10 g of isoprene are polymerized with 0,5 meq of CAT D in benzene at the temperature of 60° C. for 3 hours. After such time, 0,5 mmoli of ethyleneoxide are introduced into the reaction environment, allowing the reaction to proceed for 20'. At the end, small quantities of aqueous hydrochloric acid are added, and the polymer is isolated, which shows to contain the three hydroxyl groups per molecule.

We claim:

1. A multifunction anionic initiator of the formula

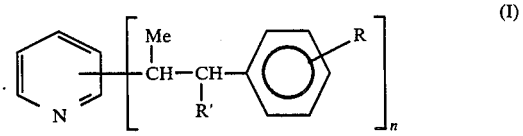

-continued or

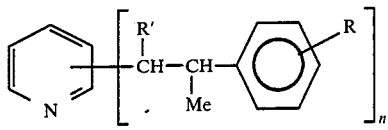
(I')

wherein
Me = an alkali metal
R' = hydrogen or a $C_{1-12}$ alkyl group; and
n = an integer of 2 or 3.

2. The multifunctional anionic initiator according to claim 1, wherein Me is lithium.

3. The multifunctional anionic initiator according to claim 1 wherein R' is a member selected from the group consisting of methyl, ethyl, n-propyl, isopropyl, n-butyl, iso-butyl, sec-butyl, tert-butyl, n-amyl, isoamyl, sec-amyl and tert-amyl.

4. The multifunctional anionic initiator according to claim 2 wherein R' is a member selected from the group consisting of methyl, ethyl, n-propyl, isopropyl, n-butyl isobutyl, sec-butyl, tert-butyl, n-amyl, isoamyl, sec-amyl and tert-amyl.

5. The multifunctional anionic initiator according to claim 1, wherein Me is lithium and R' is sec-butyl.

6. A multifunctional anionic initiator according to claim 1, wherein n is 2 and said initiator of the formula (I) or (I') is a 2,6- or 2,4-substituted pyridine compound.

7. A multifunctional anionic initiator according to claim 1, wherein n is 3 and said initiator of the formula (I) or (I') is a 2,4,6-substituted pyridine compound.

* * * * *